(12) United States Patent
Colle et al.

(10) Patent No.: US 7,417,725 B2
(45) Date of Patent: Aug. 26, 2008

(54) ILLUMINATION METHOD AND DEVICE FOR DETECTING SURFACE DEFECTS AND/OR MATERIAL SHORTAGE ON THE NECK RING OF A CONTAINER

(75) Inventors: Olivier Colle, Oullins (FR); Marc Leconte, Loire sur Rhone (FR)

(73) Assignee: TIAMA, Montagny (FR)

( * ) Notice: Subject to any disclaimer, the term of this patent is extended or adjusted under 35 U.S.C. 154(b) by 4 days.

(21) Appl. No.: 10/532,611

(22) PCT Filed: Oct. 24, 2003

(86) PCT No.: PCT/FR03/03169

§ 371 (c)(1),
(2), (4) Date: Jan. 13, 2006

(87) PCT Pub. No.: WO2004/040280

PCT Pub. Date: May 13, 2004

(65) Prior Publication Data

US 2006/0126060 A1    Jun. 15, 2006

(30) Foreign Application Priority Data

Oct. 25, 2002  (FR)  .................... 02 13358

(51) Int. Cl.
*G01N 21/90* (2006.01)
(52) U.S. Cl. ............. 356/240.1; 356/237.1; 356/239.7; 356/239.4; 250/223 B

(58) Field of Classification Search .............. 356/239.4, 356/240.1; 250/223 B
See application file for complete search history.

(56) References Cited

U.S. PATENT DOCUMENTS

| 4,606,635 | A | | 8/1986 | Miyazawa et al. |
| 4,697,076 | A | | 9/1987 | Yoshida |
| 4,775,889 | A | * | 10/1988 | Yoshida ...................... 348/127 |
| 4,975,568 | A | * | 12/1990 | Taniguchi et al. ........ 250/223 B |
| 5,072,107 | A | * | 12/1991 | Apter ...................... 250/223 B |
| 5,095,204 | A | * | 3/1992 | Novini ................... 250/223 B |
| 5,592,286 | A | | 1/1997 | Feder |
| 5,627,638 | A | * | 5/1997 | Vokhmin ..................... 356/124 |

(Continued)

FOREIGN PATENT DOCUMENTS

EP            0336476          3/1989

(Continued)

*Primary Examiner*—L. G. Lauchman
*Assistant Examiner*—Rebecca C Slomski
(74) *Attorney, Agent, or Firm*—Clark & Brody

(57) ABSTRACT

In an optical method for determining surface defects and/or material shortage on the neck ring (3) of a container having an axis of symmetry (X) comprises illuminating the surface(s) of the neck ring (3) of the container with an incident light beam, a uniform ring of light (C) is obtained that converges towards a point of convergence located on the axis of symmetry (X) of the container with a variable diameter (D) and/or variable width (E). The diameter (D) of the convergent ring of light (C) at a given value in relation to a desired mean angle of incidence ($\alpha$) to illuminate the surface of the neck ring (3) of the container and/or the width (E) of the convergent uniform ring of light (C) at a given value in relation to the width (L) of surface of the neck ring (3) of the container are selected.

15 Claims, 4 Drawing Sheets

U.S. PATENT DOCUMENTS

| | | |
|---|---|---|
| 5,923,419 A | 7/1999 | Thomas |
| 6,025,909 A * | 2/2000 | Juvinall et al. ........... 356/239.4 |
| 6,473,169 B1 * | 10/2002 | Dawley et al. ........... 356/239.4 |
| 2001/0048524 A1 * | 12/2001 | Sones ...................... 356/239.4 |
| 2006/0076475 A1 * | 4/2006 | Cochran et al. ......... 250/223 B |

FOREIGN PATENT DOCUMENTS

| | | |
|---|---|---|
| FR | 2596523 | 3/1986 |

* cited by examiner

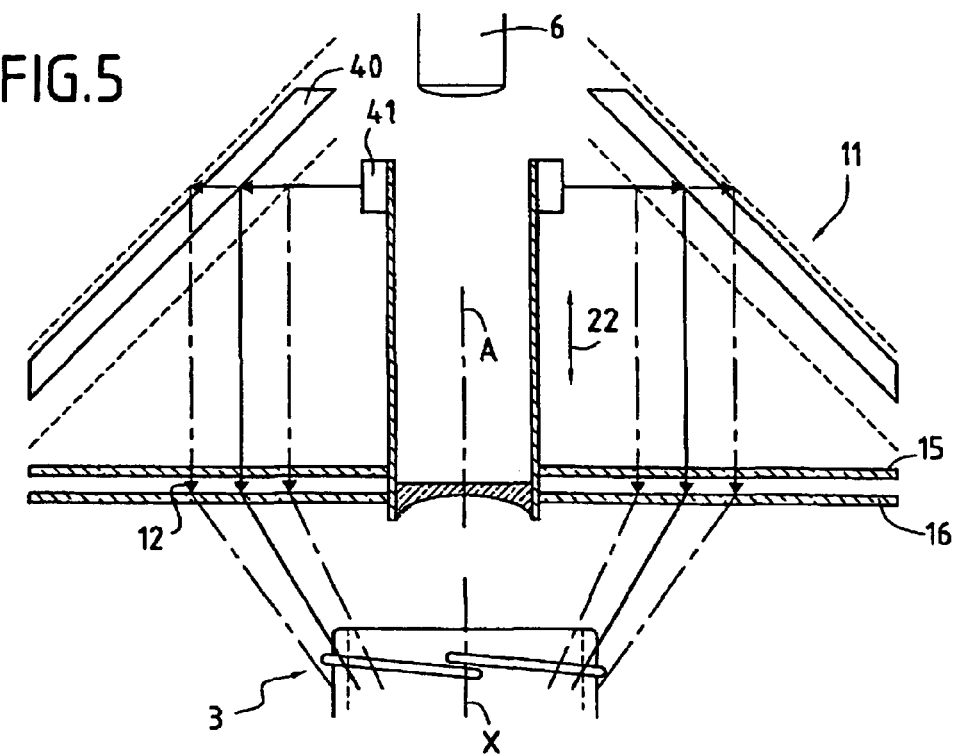
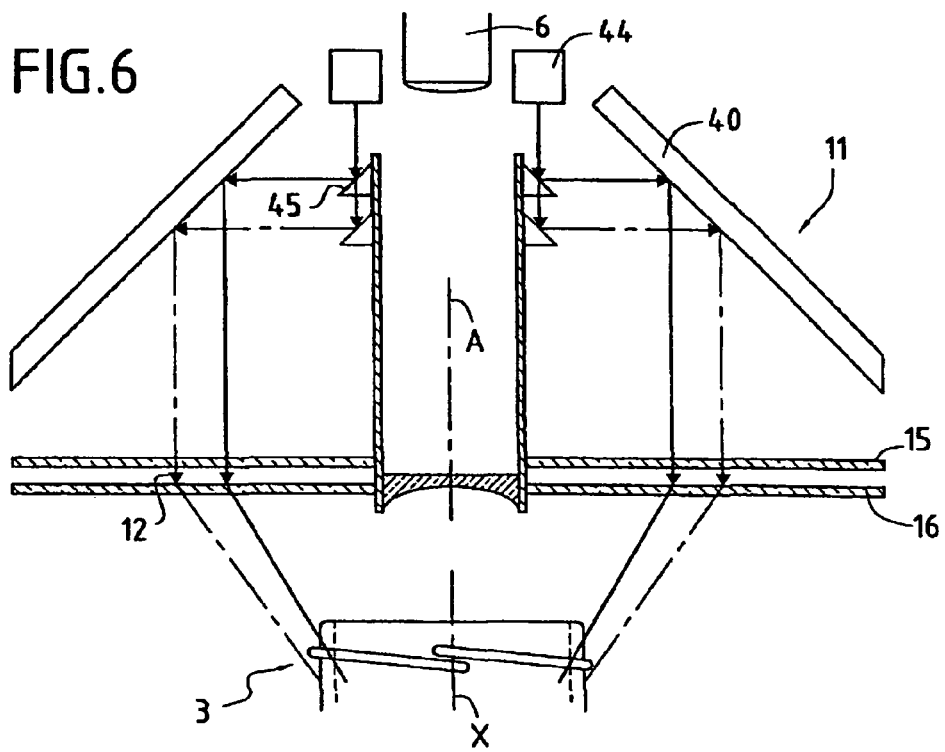

ILLUMINATION METHOD AND DEVICE FOR DETECTING SURFACE DEFECTS AND/OR MATERIAL SHORTAGE ON THE NECK RING OF A CONTAINER

FIELD OF THE INVENTION

The present invention concerns the technical area of the optoelectronical inspection of hollow objects or containers in general, that are preferably transparent or translucent such as bottles, glass jars or flasks for example, for the purpose of detecting any surface defects on the neck ring of such containers.

BACKGROUND OF THE INVENTION

The purpose of the invention is more precisely to detect, at the neck ring of an object, any surface defects or flaws corresponding to material shortage on the surface called <<unfilled finish>>.

In the state of the art, a device is known to detect such defects comprising a light source providing an incident light beam illuminating the surface of the neck ring of a container. Said detection device also comprises a line scan camera positioned to receive the light beam reflected by the neck ring of the container. The presence of a defect disturbs light reflection which, depending upon the type of defect, causes light extinction or flare detectable by the line scan camera which is connected to an analysis and processing unit adapted for analysis the video signal delivered by the camera in order to determine the presence or absence of a surface defect and/or material shortage. With said device it is possible to detect unfilled finishes in particular which relate to material shortage on the surface. An unfilled finish corresponds to a hollow part in the surface of the neck ring which is normally planar or rounded. Said defects can be see in a dark or black image against a white background.

To ensure proper inspection of the neck ring surface of containers, control must be gained over the incident angle of the light flow with respect to the surface of the neck ring. For small-sized neck rings such as those of bottles, this incident angle can be controlled by changing the height of the light source as is proposed for example in patent U.S. Pat. No. 4,606,635 which describes a device for detecting defects on the neck ring of a container. Said device comprises an annular light source delimited by an inner cylinder and an outer cylinder defining between them a cylindrical outlet whose height can be adjusted through relative movement of the cylinders. Relative movement can be imparted to this light source with respect to the container to be inspected so as to adjust the angle of incidence of the diffuse light beam.

This device is not adapted for detecting defects on neck rings having large size surface areas, in particular on account of the angle of incidence which is too small and does not allow uniform lighting of the ring surface to be obtained. Also, for containers having neck rings whose surface is slightly inclined inwards or outwards, it proves to be insufficient to correct the angle of incidence solely by adjusting the height of the light source. Finally, it is to be noted that with said inspection device it is not possible to adapt to the different diameters of the neck rings found on containers to be inspected.

Also an apparatus is known through patent FR 2 596 523 for inspecting bottle caps, comprising a divergent annular light source positioned above the cap to be inspected. This apparatus comprises a first optical mask defining the radiation range of the light source and a second optical mask defining the field of vision of a photoelectric sensor.

With this apparatus it is possible to detect a defect on the lower part of a cap on a bottle neck. However, this apparatus is not adapted for detecting defects on the surface of the neck rings of containers which all have different slopes, widths and diameters. Also, with this apparatus it is not possible to achieve uniform illumination of containers having large surface areas.

Analysis of the state of the art leads to ascertaining that a technique is required with which it is possible to control the angle of incidence and/or the width of a uniform light flow with respect to the neck ring surface of the containers, in order to adapt to the different slopes, widths and diameters of container neck rings.

BRIEF SUMMARY OF THE INVENTION

The present invention therefore sets out to meet this need by proposing a method to detect surface defects and/or material shortage on the neck rings of various containers having different slopes, widths and diameters.

To achieve this objective, the method of the invention to detect surface defects and/or material shortage, comprises the following steps:
  illuminating the surface of the container's neck ring with an incident light beam,
  collecting, via a line scan camera, the light beams reflected by the neck ring of the container to determine the presence of any surface defect and/or material shortage.

According to the invention, the method consists of:
  obtaining a uniform ring of light converging towards a point of convergence located on the axis of symmetry of the container and having a variable diameter and/or variable width,
  and of selecting:
    the diameter of the convergent uniform ring of light at a given value in relation to the desired mean angle of incidence to illuminate the surface of the neck ring of the container,
    and/or the width of the convergent uniform ring of light at a given value in relation to the surface width of the neck ring of the container.

According to one characteristic of the invention, the method consists of:
  obtaining a uniform ring of light of variable diameter and/or variable expanse,
  ensuring the convergence of the ring of light at a point of convergence, so as to illuminate the surface of the neck ring of the container with the convergent uniform light beam.

According to a first variant of embodiment, the method consists of:
  obtaining a ring of light, via a series of concentric elementary rings of light,
  selectively commanding the switching on/off of the elementary rings of light to obtain a ring of light of determined diameter and/or determined width.

According to a second variant of embodiment, the method consists of:
  obtaining a ring of light whose diameter can be varied through relative movement between a conical mirror and a planar annular light source emitting onto the conical mirror, perpendicular to the axis of said mirror,
  ensuring relative movement between the annular light source and the conical mirror along the axis of the conical mirror over a given height to obtain a ring of light of determined diameter.

According to an advantageous characteristic of the invention, the method consists of polarizing the incident light beam and of polarizing the reflected light beam before it is received by the camera.

A further objective of the invention is to propose an illumination device for a detection station detecting a neck ring surface defect and/or material shortage on a container having an axis of symmetry.

According to the invention, the illumination device comprises:
  illumination means able to provide a uniform ring of light converging towards a point of convergence located on the axis of symmetry of the container and having a variable diameter and/or variable width,
  and means for creating a convergent uniform ring of light having a given diameter value in relation to the desired mean angle of incidence to illuminate the surface of the neck ring of the container/and or a given width value in relation to the surface width of the neck ring of the container.

According to a preferred characteristic of embodiment, the illumination means comprise:
  an illumination system able to provide a uniform ring of light of variable diameter and/or variable expanse,
  and an optical system for converging the ring of light onto a point of convergence so as to illuminate the neck ring surface of the container with the convergent uniform light beam.

According to a first variant of embodiment, the illumination system, providing a ring of light, consists of a series of elementary annular light sources mounted concentric fashion with respect to each other, while the means for creating a ring of light are formed by a selective on/off command unit for the elementary annular light sources.

According to a second variant of embodiment, the illumination system, providing a ring of light of variable diameter, consists of a conical mirror movably mounted with respect to a planar annular light source emitting onto the conical mirror perpendicular to the axis of said mirror, while the means for creating a ring of light of given diameter are formed by means commanding the relative movement of the conical mirror and the planar annular light source, along the axis of the mirror and over a given height in order to obtain a ring of light of determined diameter.

According to another embodiment of the second variant of embodiment, the planar annular light source comprises an annular light source emitting in direction of a light beam return cone, along a direction perpendicular to the axis of the conical mirror, the return cone being mounted mobile or non-mobile along the axis of the conical mirror.

According to one characteristic of embodiment, the optical converging system for the ring of light is a lens of Fresnel type.

According to another characteristic of embodiment, the illumination device comprises a light diffuser placed between the optical focusing system and the annular light sources.

According to another characteristic of the invention, the illumination device comprises a polarizer placed between the illumination system and the container in order to polarize the incident light beam, and a polarizer positioned so that it can filter the reflected light beam.

According to a further characteristic of embodiment the illumination system, at the centre of its ring of light of variable diameter, comprises a sighting zone for a camera.

According to a further characteristic of embodiment the illumination system, in the camera's sighting zone, comprises a semi-reflective optical element able to transmit an additional flow of light in direction of the container to be inspected and to ensure transmission to the camera of the light beam reflected by the container.

A further objective of the invention is to propose a station for detecting surface defects and/or material shortage on the neck ring of a container having an axis of symmetry. Said detection station comprises:
  an illumination device of the invention,
  a line scan camera positioned to receive the light beam reflected by the neck ring of the container,
  and a processing and analysis unit connected to the camera and adapted to analyse the video signal delivered by the camera in order to determine the presence of a surface defect and/or material shortage.

BRIEF DESCRIPTION OF THE DRAWINGS

Various other characteristics will become apparent from the following description with reference to the appended drawings given as non-restrictive examples and showing embodiments of the subject of the invention.

FIG. 5 is a schematic elevation view of a second variant of embodiment of an illumination device of the invention.

FIG. 6 illustrates a variant of embodiment of the second embodiment illustrated in FIG. 5.

DETAILED DESCRIPTION OF THE INVENTION

Figure 1:
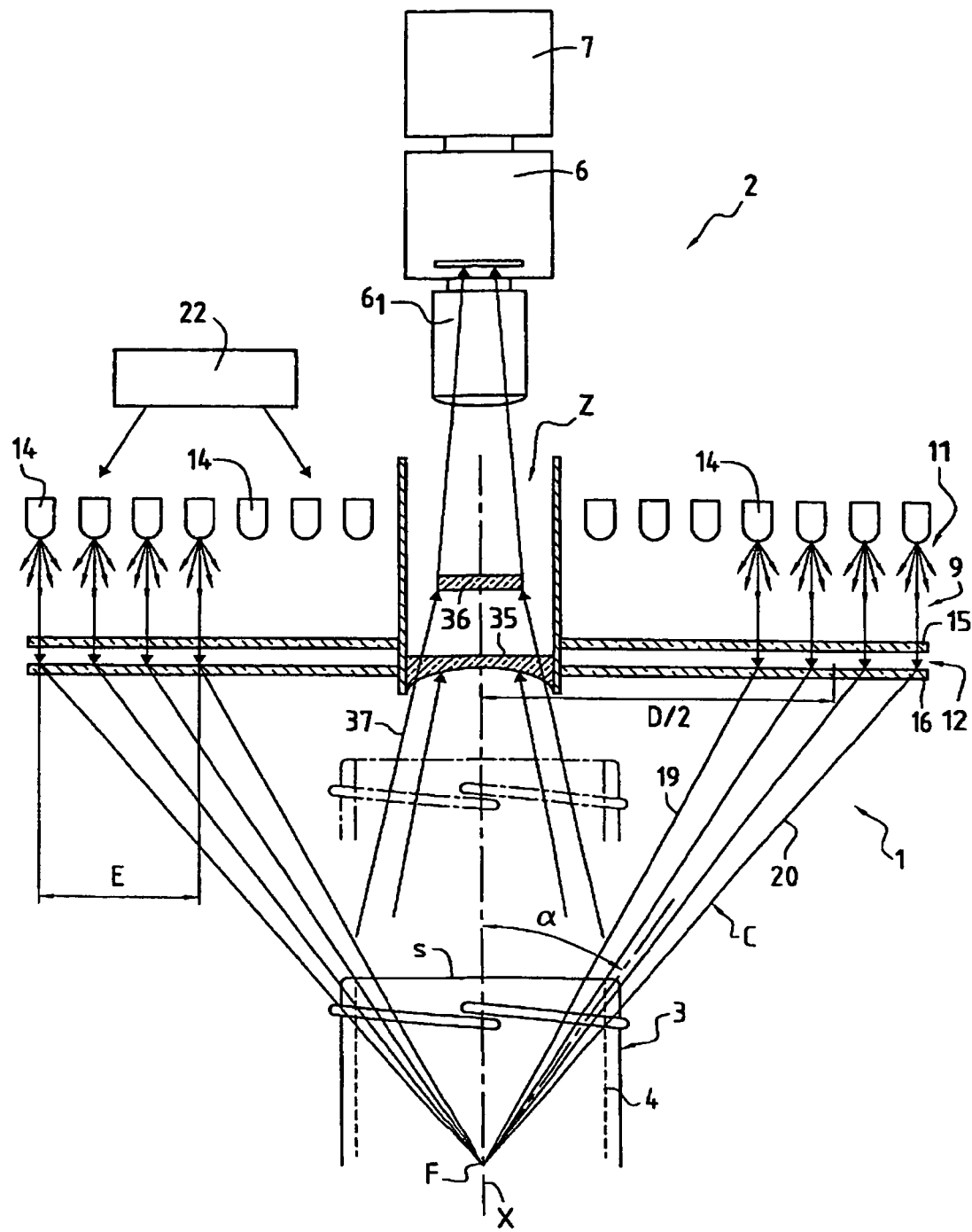
FIG. 1 is an elevation schematic showing the implementation of the method of the invention using a first variant of embodiment of the illumination device.

FIG. 1 illustrates an illumination device 1 of the invention for a surface defect and/or material shortage detection station 2 to detect possible defects on surface s of the neck ring 3 of a container 4 that is transparent or translucent for example and has an axis of symmetry or of revolution X.

In conventional manner, said detection 2 comprises a line scan camera 6, positioned to collect the light beam reflected by the surface s of the neck ring 3 of the container 4. This camera 6 is connected to an processing and analysis unit 7, adapted to analyse the video signal delivered by the camera, in order to determine the presence of a surface defect and/or material shortage on neck ring 3. The processing and analysis unit 7 will not be described in more detail since it does not come under the subject of the invention and is part of the general knowledge of persons skilled in the art.

Said detection station 2 comprising the illumination device 1 of the invention can be used to apply an optical detection method for detecting surface defects and/or material shortage on the surface of neck ring 3.

Figure 2:
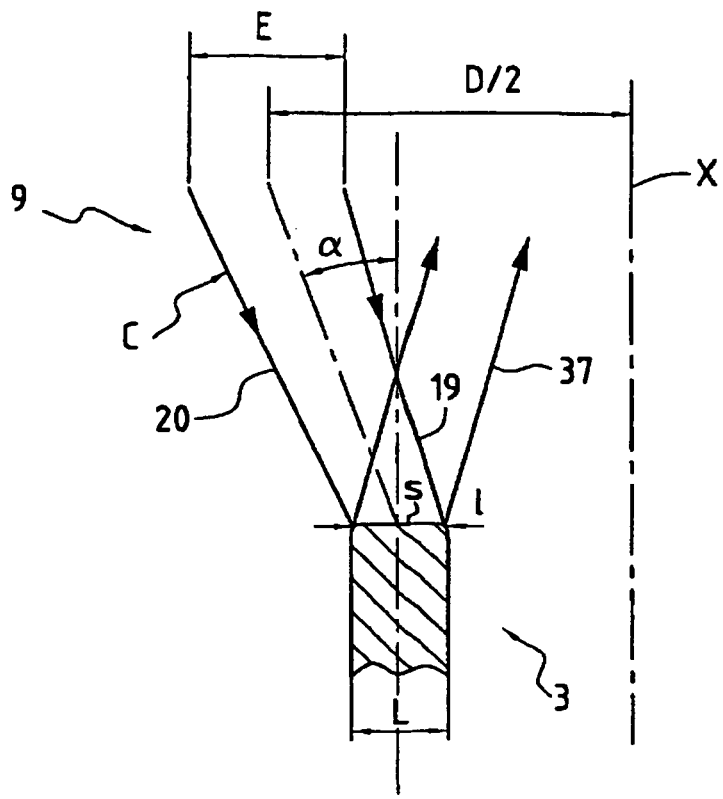
FIG. 2 is a schematic explaining the principle of the illumination method of the invention.
Figure 3:
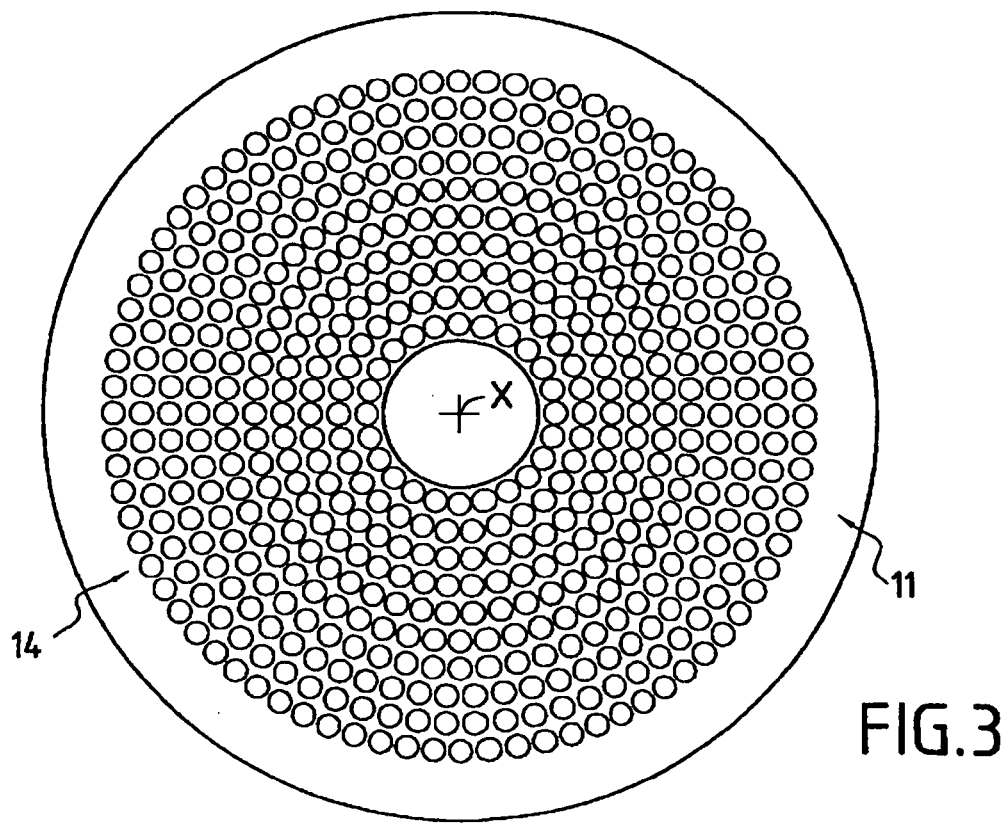
FIG. 3 is an overhead view of an example of embodiment of an illumination source used by the illumination device of the invention.

According to the invention, the illumination device 1, as can be seen more precisely in FIGS. 1 and 2, comprises illumination means 9 able to provide a uniform, convergent ring of light C converging towards a point of convergence F located on the axis of symmetry X of container 4 and having a variable diameter D and a variable width or expanse E. In the example of embodiment illustrated FIGS. 1 and 3, the illumination means 9 comprise an illumination system 11 able to provide a ring of light 12, of variable diameter D and/or variable expanse or width E. In the variant of embodiment, illustrated FIGS. 1 and 3, the illumination system 11 consists of a series of elementary annular light sources 14, totalling ten in the illustrated example, mounted concentric fashion with respect to one another, allowing a sighting zone Z to subsist in the centre for camera 6. These elementary annular light sources 14 may be tubes, fibre optic rings, or unit sources, such as electroluminescent diodes, arranged in concentric rings as illustrated FIG. 3. Each elementary annular light source 14 is therefore able to provide an elementary ring of light of given width that is identical or different to the width of the other elementary annular rings of light, and extending adjacent to one or two other elementary rings in relation to their position.

According to a preferred characteristic of embodiment, the illumination system 11 comprises a light diffuser 15 placed in front of the elementary annular sources 14, so as to obtain a uniform ring of light 12 of width or expanse E, formed from one or more elementary rings, preferably neighbouring rings. It is to be noted that FIG. 1 only shows the mean elementary light rays provided by sources 14.

According to the variant illustrated in the drawings, the illumination means 9 also comprise an optic system 16 for converging or focusing the uniform ring of light 12 onto a point of convergence F, located on the axis of symmetry X of the container, so as to illuminate the surface s of the neck ring 3 of the container with a uniform convergent light beam C. According to a preferred variant of embodiment, the optical focusing system 16 is a lens of Fresnel type. As shown in FIG. 1, the light diffuser 15 is interposed between the Fresnel 16 lens and the elementary annular sources 14.

Each uniform, convergent light beam C derived from the uniform ring of light 12, is therefore delimited between two light cones 19 and 20 having the same apex, point of convergence or focus F. This convergent light beam C therefore has a mean angle of incidence α which takes into account the mean ray of convergent beam C. Each light cone 19, 20, respectively delimiting the convergent light beam C inwardly and outwardly, therefore has a different angle of incidence α. It is to be noted that the angle of incidence α for the convergent light beam C may lie between 0 to 60° for example, preferably between 0 and 45°.

The illumination device 1 of the invention also comprises means 22 for creating a convergent, uniform ring of light C having a given diameter value D with respect to the desired mean angle of incidence α to illuminate the surface s of the neck ring 3 and/or a given expanse value E in relation to the width L of surface s of the neck ring of the container. In the example of embodiment illustrated FIGS. 1 and 3, the means 22 for creating a convergent ring of light C are formed by a selective on/off command unit for elementary light sources 14. This command unit 22 is used to selectively pilot the on/off operation of the elementary light sources 14, so as to select:

the diameter D of the ring of light 12 and subsequently the mean angle of incidence α of the convergent light beam C, and/or the width E of said beam in relation to the number of annular light sources 14 that are switched on.

In relation to the position of the elementary light source or sources that are switched on, an angle of incidence α of different values may be obtained. Similarly, provision may be made to simultaneously command the switching-on of one or more elementary light sources 14, that lie next to each other so as to act on the width or expanse E of the ring of light 12 and hence of the focused light beam C. In the example illustrated FIG. 1, the four elementary annular sources the closest to the periphery are switched on while the other sources 14 are switched off.

With said illumination device 1 it is therefore possible to obtain a convergent ring of light C with an adjustable mean angle of incidence α and/or an adjustable width E. Said adjustable angle of incidence for illumination makes it possible to adapt to the slope of neck rings 3. The width E of the convergent ring of light C enables uniform illumination to be obtained over the entire surface of the neck ring 3 of the container, irrespective of the diameter of the neck ring and the width L of the surface s of the neck ring. It is to be noted that the convergent ring of light C at the surface s of neck ring 3, has a width l that is equal to or greater than the width L of surface s of the neck ring.

It is to be noted that container 4 may be moved along its axis of symmetry X, in order to adjust the position of surface s of the neck ring with respect to the convergent light beam C.

According to an advantageous characteristic of embodiment, the illumination device 1 comprises a polarizer, not shown, interposed between the illumination system 11 and the container 4, in order to polarize the incident light beam C. Preferably, the light beam C is polarized circularly by a circular polarizer mounted between the Fresnel lens 16 and the container 4. A polarizer, of same circular type as the one used for the incident beam, is placed in front of the lens of camera 6 to filter the reflected light beam. The light, reflected on the surface of neck ring 3, is not depolarized and therefore passes without being attenuated through the polarizer placed in front of the lens of camera 6. On the other hand, stray light which has undergone multiple reflections inside container 4 is partly depolarized and is hence attenuated when passing through the polarizer placed in front of the camera. Said polarization makes it possible to attenuate stray light with respect to the incident illumination light.

As can be clearly seen FIG. 1, the illumination means 9, in the centre of their ring of light 12, comprise a sighting zone Z for camera 6. This sighting zone 2 is arranged in the centre of the illumination system 1 which in this zone does not comprise elementary annular light sources 14. For example, this sighting zone Z may be occupied by a divergent lens 35 forming a first image 36 of the neck ring 3 taken up by a variable focus system $6_1$ such as a short focusing zoom, associated with the camera 6.

Figure 4:
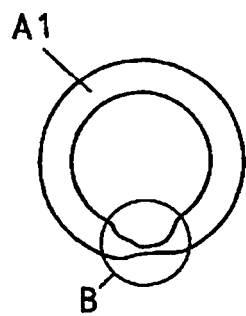
FIG. 4 is an example of an image obtained using the method of the invention.

The illumination device 1 of the invention is particularly adapted to allow detection of defects on the surface s of neck rings of containers, in particular unfilled finishes through material shortage. As can be seen FIG. 4, the flow of light 37 reflected by the surface s of a neck ring gives a ring of light A1 which, when there is a material shortage defect on the surface of neck ring 3, has a dark area B corresponding to the defect.

It is to be considered that any defect occurring on surface s causes either lack of light or local concentration of light translating as a dark spot flare that is detectable by the processing and analysis unit 7.

FIG. 5 illustrates a second variant of embodiment of the illumination system 11 providing a uniform ring of light 12 of variable diameter. According to this variant, the illumination system 11 consists of a conical mirror 40 which in the illustrated example has a polished inner surface. The illumination system 11 also comprises a planar annular light source 41 emitting onto the conical mirror and more precisely onto the polished inner surface, perpendicular to axis A of the conical mirror 40 which is co-linear with the axis of symmetry X of the container. The conical mirror 40 and the annular light source 41 are movably mounted with respect to one another along axis A of the conical mirror 40.

According to this variant of embodiment, the means 22 for creating a ring of light 12 of given diameter are formed by command means commanding the relative movement of the conical mirror 40 and the planar annular light source 41. These command means 22 ensure the relative movement of the conical mirror 40 and the planar annular light source 41 along axis A of the conical mirror 41 and over a given height in order to obtain a ring of light 12 of determined diameter. Evidently, provision may be made to move either the conical mirror 40, or the light source 41 or both.

In the illustrated example of embodiment, the planar light source 41 may be made in different manners, for example using an optic fibre, bulb, fluorescent tube, electroluminescent diodes, etc. Also, the annular light beam, as explained in the example illustrated FIG. 1, is directed towards the light diffuser 15 and the Fresnel lens 16.

FIG. 6 illustrates another variant of embodiment, in which the planar annular light source 41 consists of an annular light source 44, emitting along a direction substantially parallel to axis A of conical mirror 40, in the direction of a return cone 45 returning the light beam in a direction perpendicular to the axis of conical mirror 40. The return cone 45 may be mounted mobile fashion in relation to the conical mirror so as to obtain a ring of light 12 of variable diameter. Evidently, provision may also be made to mount the return cone 45 in fixed manner, while the conical mirror 40 is movably mounted as explained above.

It is to be noted that in the examples of embodiment illustrated FIGS. 5 and 6, the light source 41, 44 emits onto the inner surface of a conical mirror 40. Evidently, it may be contemplated that the light source sends its beam onto the outer polished surface of the conical mirror 41, reversing the direction of the conical mirror 40.

It is to be noted that the assembly illustrated FIG. 6 also makes it possible to adjust the expanse E of the ring of light 12. Insofar as the annular light source 44 is divergent, (for example at an angle of 60° for an optic fibre), expanse E of the ring of light 12 projected onto the light diffuser 15 varies when the length of the optic pathway of the light rays is modified between source 44 and diffuser 15, passing through the return cone 45 and the conical mirror 40. Said modification of the optic pathway of the light rays may be obtained by moving source 44 along axis A of the mirror.

Figure 7:
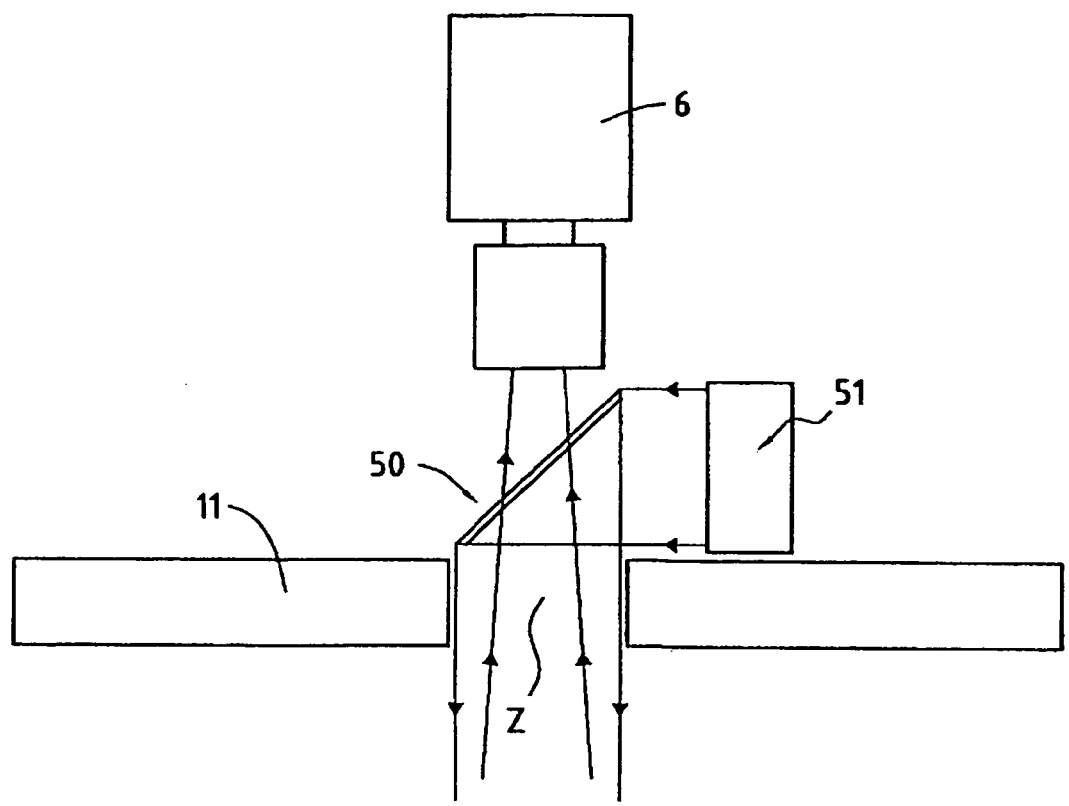
FIG. 7 illustrates a further characteristic of the illumination device of the invention.

FIG. 7 illustrates a preferred variant of embodiment of the illumination device 1 in which provision is made to produce additional illumination with rays parallel or almost parallel to axis X of the container having regard to the presence of the sighting zone Z for camera 6. This sighting zone Z, located in the centre of the illumination means 9, does not make it possible to obtain light rays with corresponding angles of incidence. According to this variant of embodiment, an additional light beam is provided in this sighting zone Z, in order to obtain angles of incidence that are complementary with respect to those obtained with the uniform ring of light 12.

According to this example of embodiment, the illumination system 11 in its sighting zone Z, comprises a semi-reflective optical element 50, such as a semi-reflective strip able to transmit an additional flow of light along a direction parallel to axis X in the direction of container 4, and derived from an additional light source 51. The semi-reflective optical element 50 enables the transmission to camera 6 of the light beam 37 reflected by container 4.

The invention is not limited to the examples shown and described since various modifications may be made thereto without departing from the scope of the invention.

The invention claimed is:

1. Optical method for determining surface defects and/or material shortage on the neck ring (3) of a container (4) having an axis of symmetry (X), the method comprising the following steps:
   illuminating the surface(s) of the neck ring (3) of the container (4) with a uniform ring of light,
   and collecting, via a line scan camera (6), the light beams reflected by the neck ring of the container, in order to determine the presence of a surface defect and/or material shortage, the illuminating step causing the surface defect to occur as a lack of light or local concentration of light translating as a dark spot,
   characterized in that it consists of:
      obtaining the uniform ring of light (C) delimited between two light cones (19 and 20), the uniform ring of light converging towards a point of convergence (F) located on the axis of symmetry (X) of the container, and having a variable diameter (D) and/or a variable width (E),
      and selecting:
         the diameter (D) of the convergent ring of light (C) at a given value in relation to a desired mean angle of incidence (α) to illuminate the surface (s) of the neck ring (3) of the container (4),
         and/or the width (E) of the convergent uniform ring of light (C) at a given value in relation to the width (L) of the surface(s) of the neck ring (3) of container (4).

2. Method as in claim 1, characterized in that it consists of:
   obtaining a ring of light (12), via a series of elementary concentric rings of light (14),
   and selectively commanding the switching on/off of the elementary rings of light (14) in order to obtain a ring of light (12) of determined diameter (D) and/or of determined width (E).

3. Method as in claim 1, characterized in that it consists of:
   obtaining a ring of light (12) of variable diameter through the relative movement of a conical mirror (40) in relation to a planar annular light source (41, 44) emitting onto the conical mirror, perpendicular to the axis (A) of said mirror,
   and ensuring relative movement between the annular light source (41, 44) and the conical mirror (40) along axis (A) of the conical mirror (40) over a given height to obtain a ring of light of determined diameter.

4. Method as in claim 1, characterized in that it consists of polarizing the uniform ring of light and of polarizing the reflected light beam before it is received by the camera (6).

5. Illumination device for a detection station to detect surface defects and/or material shortage on the neck ring (3) of a container (4) having an axis of symmetry (X), characterized in that it comprises:
   illumination means (9) able to provide a uniform ring of light (C) delimited between two light cones (19 and 20), the uniform ring of light converging towards a point of convergence (F) located on the axis of symmetry (X) of the container, and having a variable diameter (D) and/or a variable width (E), the illumination means (9) causing the surface defect to occur as a lack of light or local concentration of light translating as a dark spot,
   and means (22) for converging the uniform ring of light (C) to have a given diameter value (D) in relation to the desired mean angle of incidence (α) to illuminate the surface of the neck ring of the container and/or a width (E) of given value in relation to the width (1) of the surface(s) of the neck ring (3) of container (4).

6. Device as in claim 5, characterized in that the illumination means (9) comprise:
- an illumination system (11) able to provide a uniform ring of light (12) of variable diameter and/or of variable expanse (E),
- and an optical focusing system (16) for converging the ring of light (12) onto a point of convergence (F) so as to illuminate the surface(s) of the neck ring (3) of the container with the convergent uniform light beam (C).

7. Device as in claim 5, characterized in that the illumination system (11), providing a ring of light (12), consists of a series of elementary annular light sources (14) mounted concentric fashion with respect to one another, and in that the means (22) for creating a ring of light (12) are formed by a selective switch on/off command unit for the elementary annular light sources (14).

8. Device as in claim 5, characterized in that the illumination system (11), providing a ring of light (12) of variable diameter consists of a conical mirror (40) movably mounted with respect to a planar annular light source (41) emitting onto the conical mirror perpendicular to the axis of said mirror, and in that the means (22) for creating a ring of light of given diameter are formed by means commanding the relative movement of the conical mirror (40) in relation to the planar annular light source (41), along the axis of the mirror and over a given height to obtain a ring of light of determined diameter.

9. Device as in claim 8, characterized in that the planar annular light source comprises an annular light source (44) emitting in the direction of a return cone (45), which returns the beam of light, along a direction perpendicular to the axis of the conical mirror, the return cone (45) being mounted mobile or non-mobile fashion on the axis of the conical mirror.

10. Device as in claim 5, characterized in that the optical convergence system (16) for the ring of light is a lens of Fresnel type.

11. Device as in claim 5, characterized in that it comprises a light diffuser (15) positioned between an optical focusing system (16) and the annular light sources (14, 41, 44).

12. Device as in claim 5, characterized in that it comprises a polarizer interposed between the illumination system and the container to polarize the incident light beam, and a polarizer positioned to filter the reflected light beam.

13. Device as in claim 5, characterized in that the illumination system (11), at the centre of its ring of light (12) of variable diameter, comprises a sighting zone (Z) for a camera (6).

14. Device as in claim 13, characterized in that in the camera's sighting zone (Z) it comprises a semi-reflective optical element (50) able to transmit an additional flow of light in the direction of the container to be inspected (4) and to ensure the transmission to camera (6), of the light beam reflected by the container.

15. Detection station to detect surface defects and/or material shortage on the neck ring of a container (4) having an axis of symmetry (X), characterized in that it comprises:
- an illumination device (1) as in claim 6,
- a line scan camera (6) positioned so as to receive the light beam reflected by the surface of the neck ring of the container, and a processing and analysis unit (7) connected to camera (6) and adapted to analyse the video signal delivered by the camera in order to determine the presence of any surface defect and/or material shortage.

* * * * *